US005620456A

United States Patent [19]
Sauer et al.

[11] Patent Number: 5,620,456
[45] Date of Patent: Apr. 15, 1997

[54] TROCAR ASSEMBLY

[75] Inventors: Jude S. Sauer, Pittsford; Roger J. Greenwald, Holley; Mark A. Bovard, Palmyra; Thomas A. Tiberio, Webster, all of N.Y.

[73] Assignee: Lasersurge, Inc., Rochester, N.Y.

[21] Appl. No.: 546,168

[22] Filed: Oct. 20, 1995

[51] Int. Cl.$^6$ ............................................. A61B 17/34
[52] U.S. Cl. ...................... 606/185; 606/170; 604/164; 604/264
[58] Field of Search ................... 128/754, 751; 604/22, 164, 264; 606/167, 171, 185, 170, 174; 30/173, 175, 187

[56] References Cited

U.S. PATENT DOCUMENTS

| | | | |
|---|---|---|---|
| 3,538,916 | 11/1970 | Wiles et al. | |
| 3,809,095 | 5/1974 | Cimber. | |
| 3,915,169 | 10/1975 | McGuire. | |
| 4,461,305 | 7/1984 | Cibley. | |
| 4,559,041 | 12/1985 | Razi | 604/157 |
| 4,667,684 | 5/1987 | Leigh | 128/754 |
| 4,733,671 | 3/1988 | Mehl | 128/754 |
| 4,962,770 | 10/1990 | Agee et al. | 128/898 |
| 4,976,269 | 12/1990 | Mehl | 128/754 |
| 4,991,600 | 2/1991 | Taylor | 128/754 |
| 5,089,000 | 2/1992 | Agee et al. | 606/170 |
| 5,116,353 | 5/1992 | Green | 606/184 |
| 5,224,951 | 7/1993 | Freitas | 606/172 |
| 5,312,354 | 5/1994 | Allen et al. | 604/164 |
| 5,314,417 | 5/1994 | Stephens et al. | 604/264 |
| 5,372,588 | 12/1994 | Farley et al. | 604/164 |

*Primary Examiner*—Michael Buiz
*Assistant Examiner*—Patrick W. Rasche
*Attorney, Agent, or Firm*—Cumpston & Shaw

[57] ABSTRACT

An obturator assembly for penetrating body tissue, includes a handle assembly having a finger-actuated trigger member, a sleeve member connected to and extending from the handle assembly, an obturator shaft at least partially positioned within the sleeve member and engageable with the finger-actuated trigger member of the handle assembly and a cutting mechanism supported by the distal end portion of the obturator shaft. The cutting mechanism is deployable for cutting action upon movement of the trigger member. A method of using the obturator assembly is also disclosed.

35 Claims, 14 Drawing Sheets

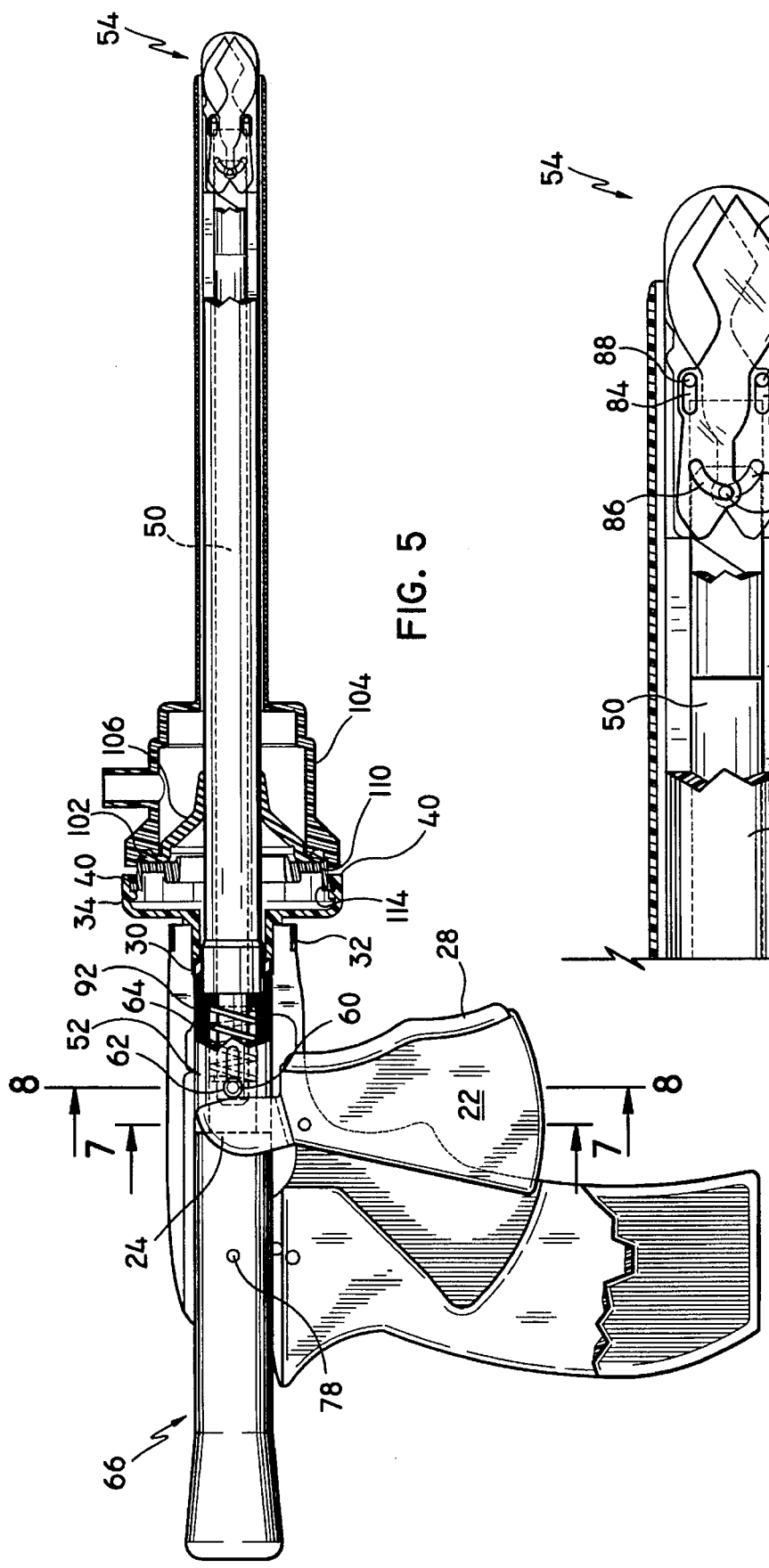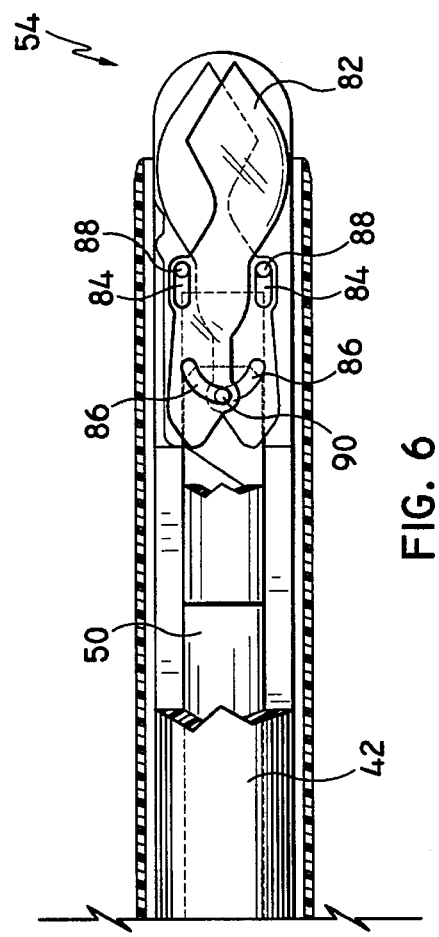

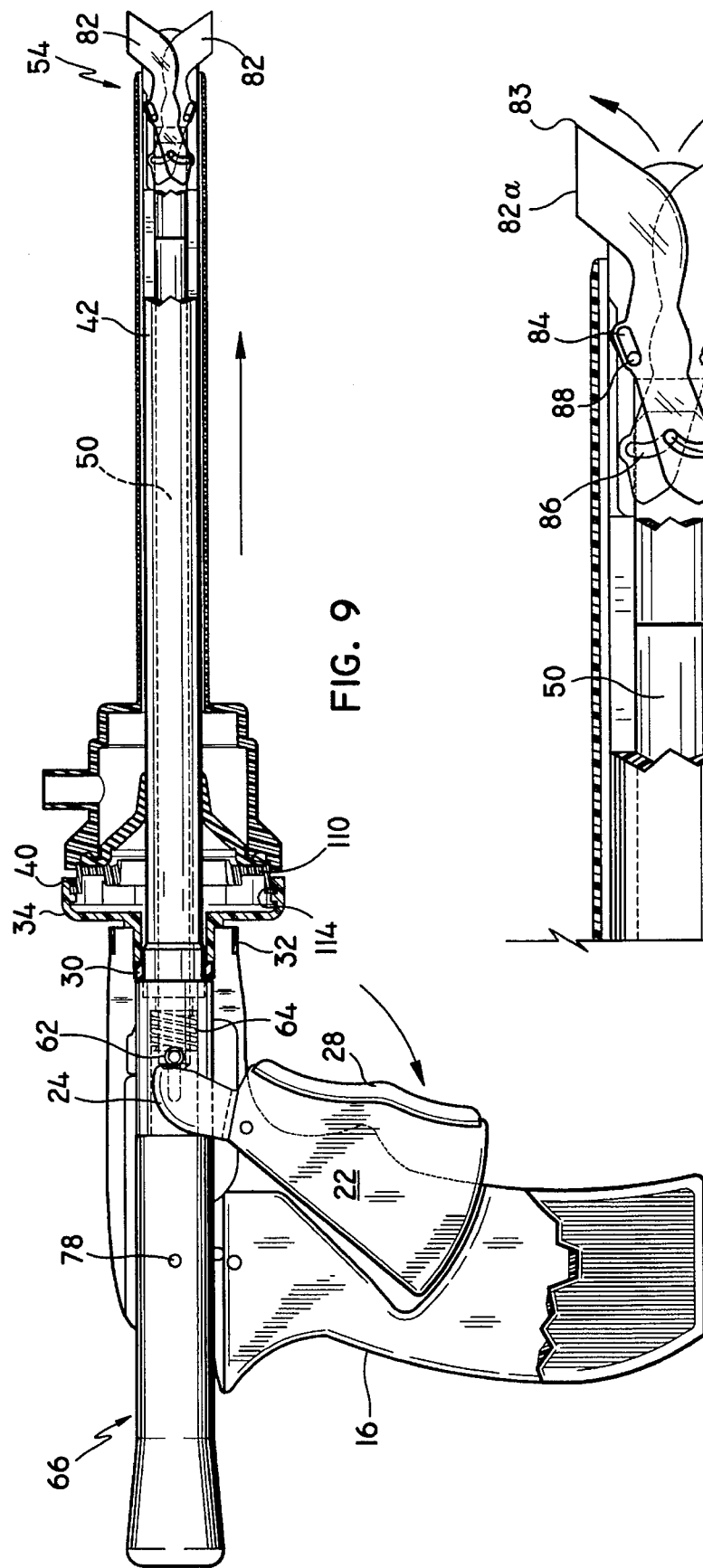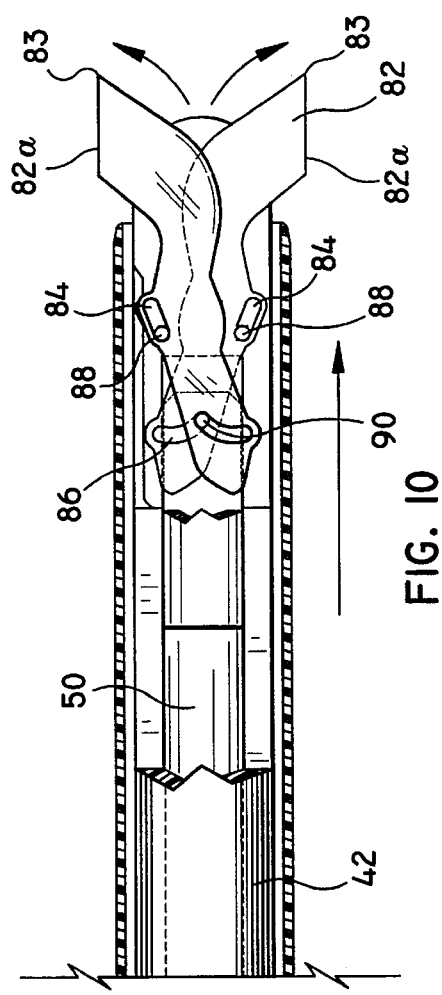

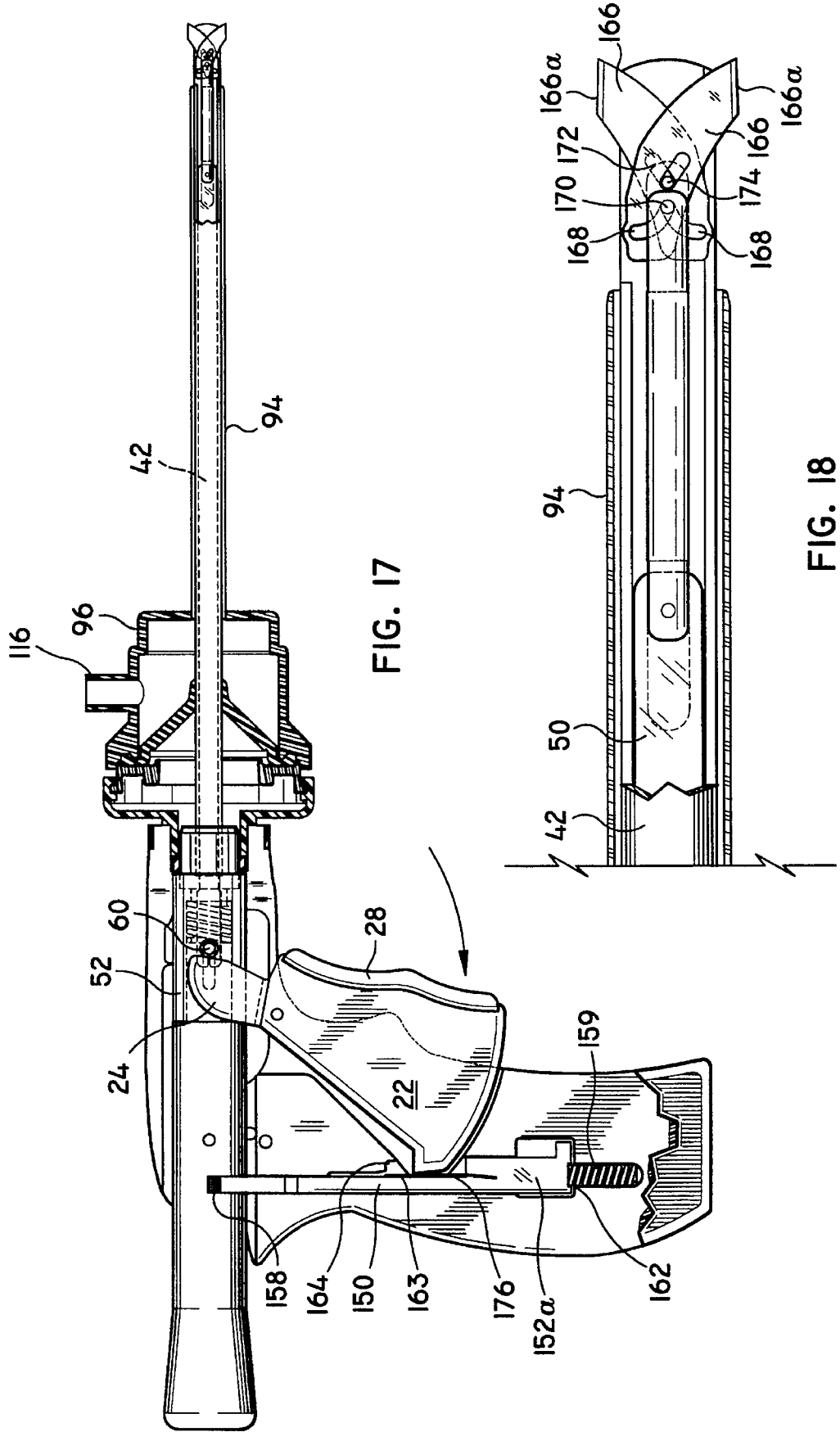

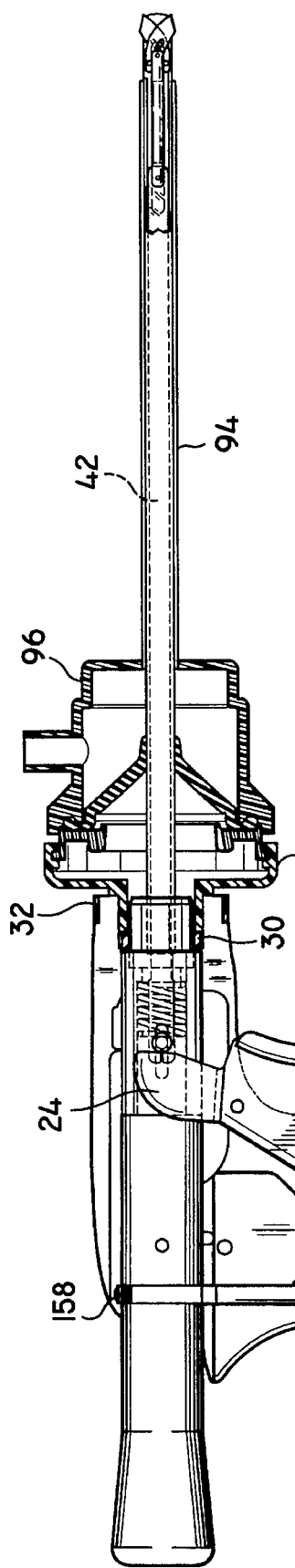
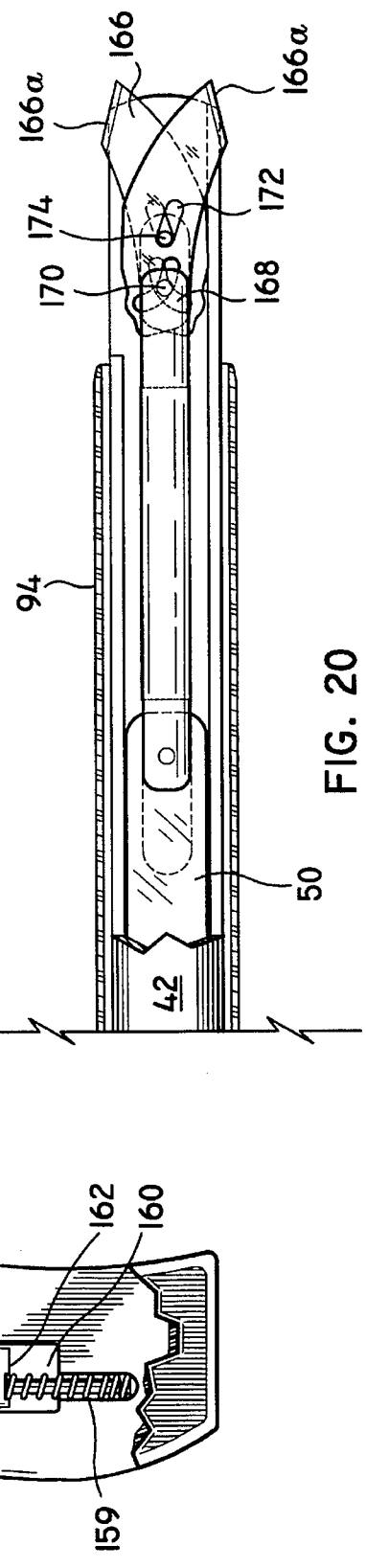
FIG. 19
FIG. 20

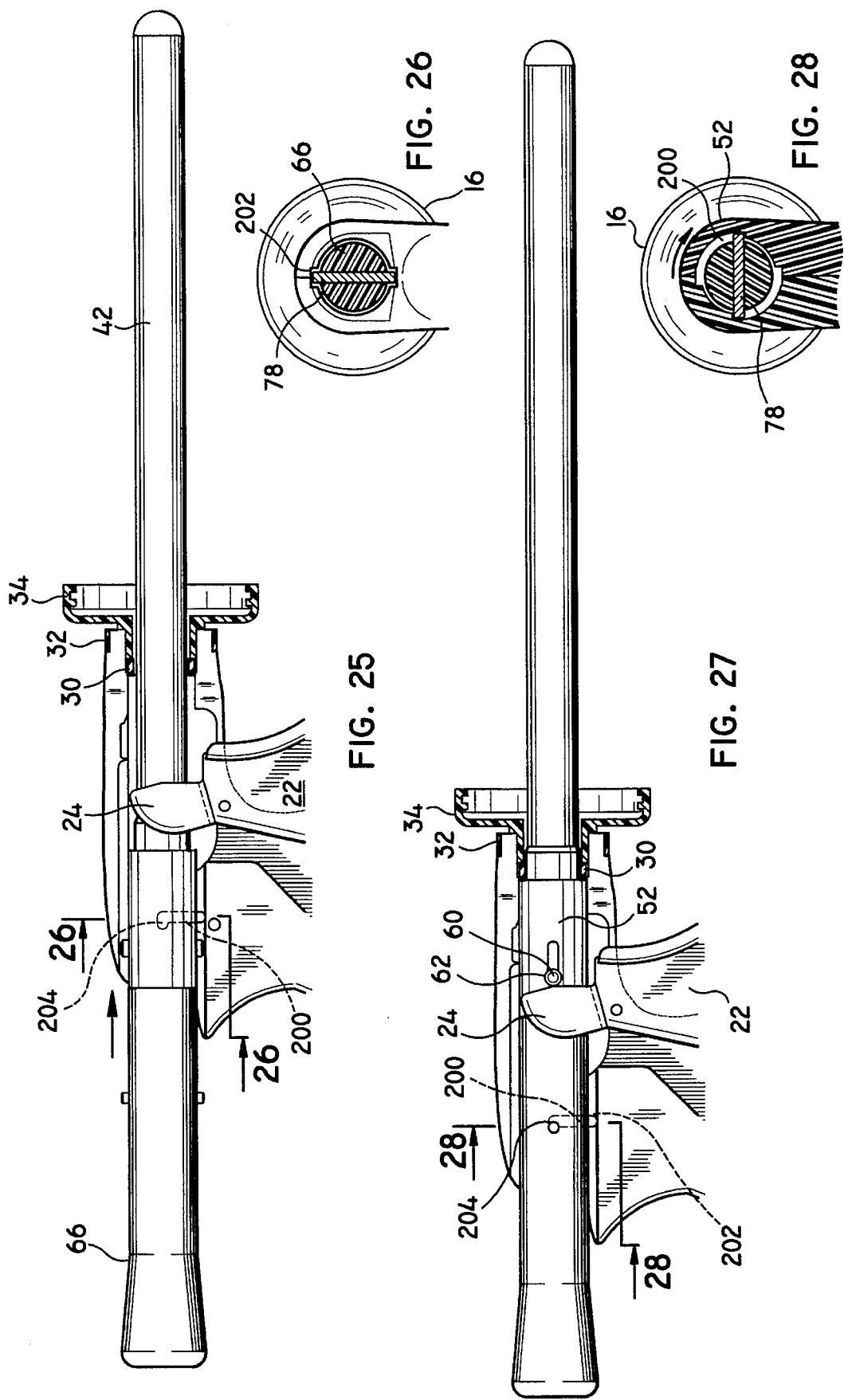

TROCAR ASSEMBLY

BACKGROUND

1. Technical Field

The present disclosure relates to an apparatus for penetrating body tissue, and, more particularly, to a trocar having an obturator responsive to actuation of a trigger mechanism. The present disclosure further relates to a handle assembly to which various ports, trocars and other devices can be attached and which incorporates a trigger mechanism that can drive several different functions of the various attachments.

2. Description of Related Art

Endoscopic surgical procedures, that is, surgical procedures performed through tubular sleeves or cannulas, have been utilized for many years. Initially, endoscopic surgical procedures were primarily diagnostic in nature. More recently as endoscopic technology has advanced, surgeons are performing increasingly complex and innovative endoscopic surgical procedures. In endoscopic procedures, surgery is performed in any open space in the body through natural openings, a small incision or through narrow endoscopic tubes (cannulas) inserted through small entrance wounds in the skin. In laparoscopic procedures, surgery is performed in the interior of the abdomen.

Laparoscopic procedures generally utilize instrumentation that is internally sealed to inhibit gases from entering or exiting the body through the laparoscopic or endoscopic incision. This is particularly true in surgical procedures in which the surgical region is insufflated. Moreover, laparoscopic and endoscopic procedures often require the surgeon to act on organs, tissues and vessels far removed from the incision, thereby requiring that any instruments to be used in such procedures be of sufficient size and length to permit remote operation.

In accordance with laparoscopic surgical procedures, the abdominal cavity is insufflated with a suitable gas such as $CO_2$. Thereafter, a trocar is employed to puncture the abdominal wall. Generally, a conventional trocar includes an obturator having a sharp obturator tip for penetrating the body cavity and a protective sleeve in which the obturator is coaxially positioned. The trocar also includes or, is used in combination with, a cannula which remains in place for use during the surgery. An example of a known trocar is described in commonly assigned U.S. Pat. No. 4,601,710 to Moll.

Although conventional trocars have been generally effective for their intended purposes, it has become apparent that certain improvements and modifications can be made to existing trocars to more adequately adapt the trocar for laparoscopic surgery. In particular, one disadvantage with known trocars and their uses concerns the difficulty encountered by the surgeon in controlling the penetrating movement of the trocar through the body wall as well as the force required on behalf of the surgeon to achieve such penetration. In applying a conventional trocar, the surgeon typically grasps the proximal end or housing portion of the trocar and exerts a downward force to cause penetration of the obturator tip through the body tissue, e.g., the abdominal wall and peritoneal lining. Since the force required to achieve penetration through the abdominal wall is relatively high, e.g., 5–15 lbs., the momentum generated during such penetration may carry the obturator tip into engagement with underlying tissue or viscera if the surgeon is not careful.

Another disadvantage with known trocars is that prior to application of the trocar an incision must be made with a scalpel or similar instrument in the outer skin tissue to facilitate the subsequent positioning of the trocar and penetrating movement into the abdominal cavity. Thus, the requirement of the incision adds another step and device to the surgical procedure. Moreover, often times the incision is imprecise in that it is inappropriately too large or too small for the obturator tip. An oversized incision will negatively affect the integrity of the seal formed about the cannula with the adjacent body tissue and may increase the risk of bleeding at the incision site. An undersized incision will result in possible tissue tear during application and penetration of the obturator tip. Even further, the undersized tissue can ultimately lead to necrosis of the tissue compressed around the cannula by stopping the blood flow.

A further disadvantage with known trocars concerns the shape and dimension of the formed incision. The obturator tip of a conventional trocar typically is pyramidally-shaped which provides an arcuate incision or opening in the body cavity wall. An arcuate incision or opening is less desirable than a linear incision since an arcuate incision generally entails a lengthier recovery time and does not heal as neatly as compared to linear incisions.

Accordingly, there exists a need for a trocar incorporating structure which enhances control of the trocar and which facilitates the penetrating action of its penetrating tip. There also exists a need for a trocar having tissue cutting structure which obviates the need for an initial incision to be made in the outer skin tissue with a separate device. There further exists a need for a trocar having tissue cutting structure which forms a generally linear incision in the body wall. There further exists a need for a trocar that is capable of both sharp and blunt dissection.

SUMMARY

Generally stated, the present invention is directed to an obturator assembly for penetrating body tissue. The obturator assembly includes a handle assembly having a finger-actuated trigger member, a sleeve member connected to and extending from the handle assembly, an obturator shaft at least partially positioned within the sleeve member and engageable with the trigger member of the handle assembly and a cutting mechanism disposed at the distal end portion of the obturator shaft and being deployable for cutting action upon movement of the trigger member. The obturator shaft is adapted to move distally upon movement of the trigger member to deploy the cutting mechanism from the sleeve member.

The preferred cutting mechanism includes first and second blade members. The blade members are at least moveable relative to the longitudinal axis of the obturator shaft between a first non-deployed position wherein the cutting blades are disposed within the obturator sleeve and a second deployed position wherein cutting edges of the cutting blades are displaced relative to the longitudinal axis and exposed beyond the obturator sleeve. The cutting edges of the cutting blades move substantially within a common plane to thereby form a linear incision in body tissue. A camming mechanism is provided to effectuate deployment of the cutting blades.

The obturator is also advantageously configured to perform blunt dissection of some of the layers of the abdominal wall when the cutting blades are in the non-deployed position.

The present invention is also directed to a surgical trocar including a cannula and an obturator configured for at least partial insertion into the cannula. The obturator includes an obturator shaft reciprocally axially movable within the cannula, at least two blade members supported at a distal end portion of the obturator and moveable between at least a non-deployed position and a fully deployed position in response to movement of the obturator shaft and a handle operatively connected to the obturator shaft and having a trigger selectively movable to cause reciprocal axial movement of the obturator shaft and movement of the blade members between the non-deployed and fully deployed positions thereof. The trocar may further include a manually operable member mounted to the handle and operatively engageable with the trigger. The manually operable member is selectively movable between two positions. In a first position of the manually operable member, the trigger is capable of moving to a first position thereof corresponding to the fully deployed position of the blade members. In a second position of the manually operable member the trigger can only be partially moved to a second position thereof corresponding to a partially deployed position of the cutting blades. The manually operable member enables the surgeon to effectively control the dimension of the incision formed in body tissue. This is a significant feature, particularly, in laparoscopic surgery, where as will be appreciated from the foregoing description, it may be desirable to form an incision in the outer skin of the abdomen which is greater in dimension than the incision formed in the abdominal wall or peritoneal lining.

The present disclosure is also directed to a handle system for a surgical device.

BRIEF DESCRIPTION OF THE DRAWINGS

Various embodiments of the present disclosure are described hereinbelow with reference to the drawings wherein:

FIG. 5 is a side plan view in partial cross-section of the surgical trocar of FIG. 1 in an initial unactuated position;

FIG. 6 is an enlarged side plan view in cross-section of the distal end of the obturator assembly illustrating the arrangement of the cutting blades prior to deployment;

FIG. 9 is a view similar to the view of FIG. 5 illustrating the surgical trocar actuated with the distal blade members in a deployed position;

FIG. 10 is a view similar to the view of FIG. 6 further illustrating the cutting blades in the deployed position;

FIG. 17 is a view similar to the view of FIG. 15 illustrating the switch in a first downward position and the handle actuated to fully deploy the cutting blades;

FIG. 18 is an enlarged side plan view in cross-section of the distal end of the obturator assembly illustrating the cutting blades in the fully deployed position;

FIG. 19 is a view similar to the view of FIG. 15 illustrating the switch in a second upward position and the handle actuated to deploy the cutting blades to an intermediate cutting position;

FIG. 20 is a view similar to the view of FIG. 18 further illustrating the cutting blades in the intermediate cutting position;

FIG. 25 is a side plan view of the obturator assembly with one-half of the handles removed illustrating insertion of the obturator portion into the handle;

FIG. 26 is a cross-sectional view taken along the lines 26—26 of FIG. 25;

FIG. 27 is a view similar to the view of FIG. 25 illustrating the obturator portion mounted within the handle; and FIG. 28 is a cross-sectional view taken along the lines 28—28 of FIG. 27.

DETAILED DESCRIPTION OF PREFERRED EMBODIMENT(S)

Figure 1:
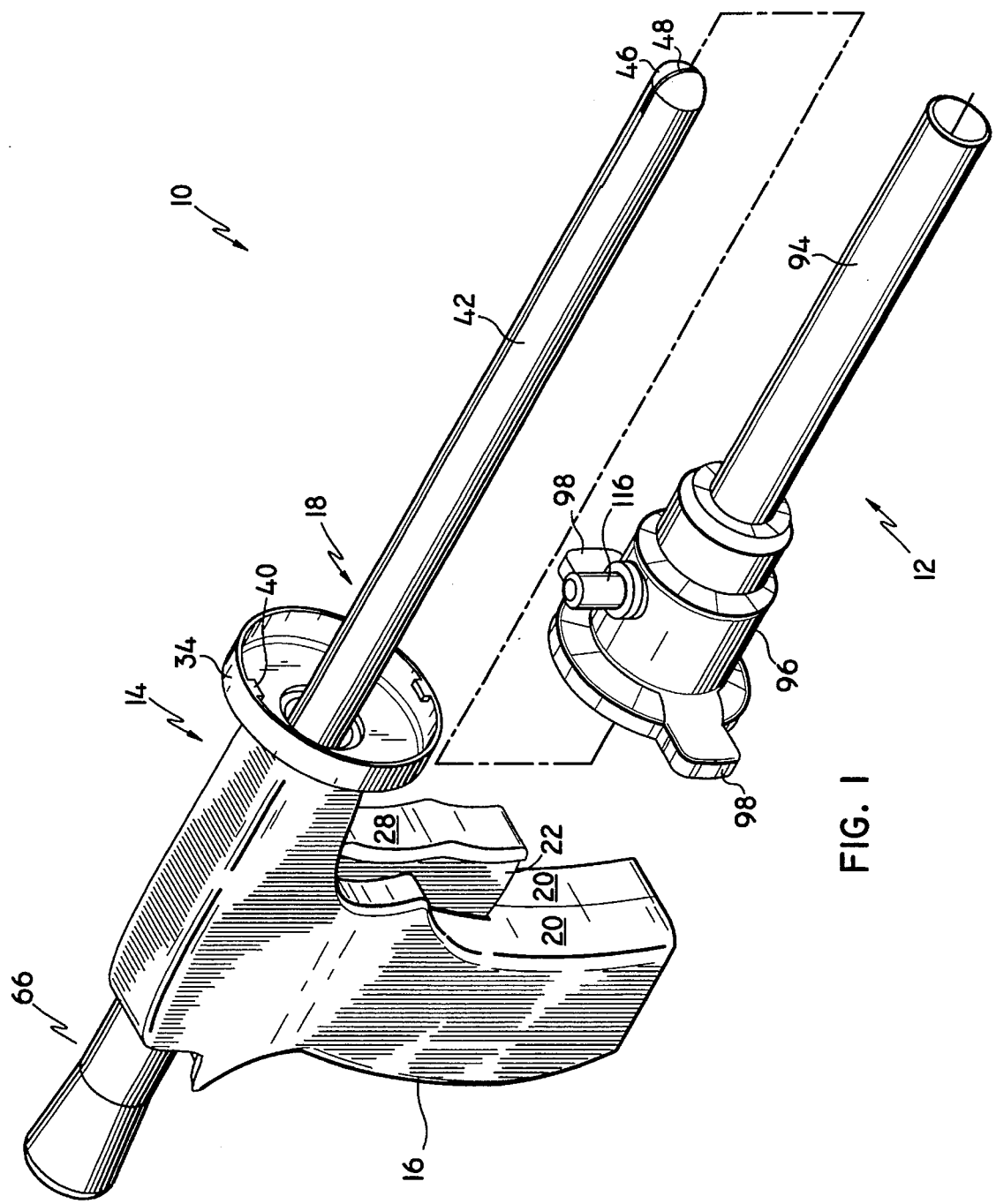
FIG. 1 is a perspective view of the surgical trocar of the present disclosure consisting of a trigger actuated obturator assembly and a cannula assembly.

The trocar assembly of the present disclosure is intended to penetrate body tissue, e.g., the abdominal wall of a patient, with minimal exertion force required on behalf of surgical personnel. Referring initially to FIG. 1, the trocar assembly 10 includes a cannula assembly 12 and an obturator assembly 14 which is at least partially positionable within the cannula assembly 12. The term obturator assembly as used herein refers to the tissue penetrating portion of the trocar assembly 10. The obturator assembly 14 will be initially discussed followed by a discussion of the cannula assembly 12.

Figure 2:
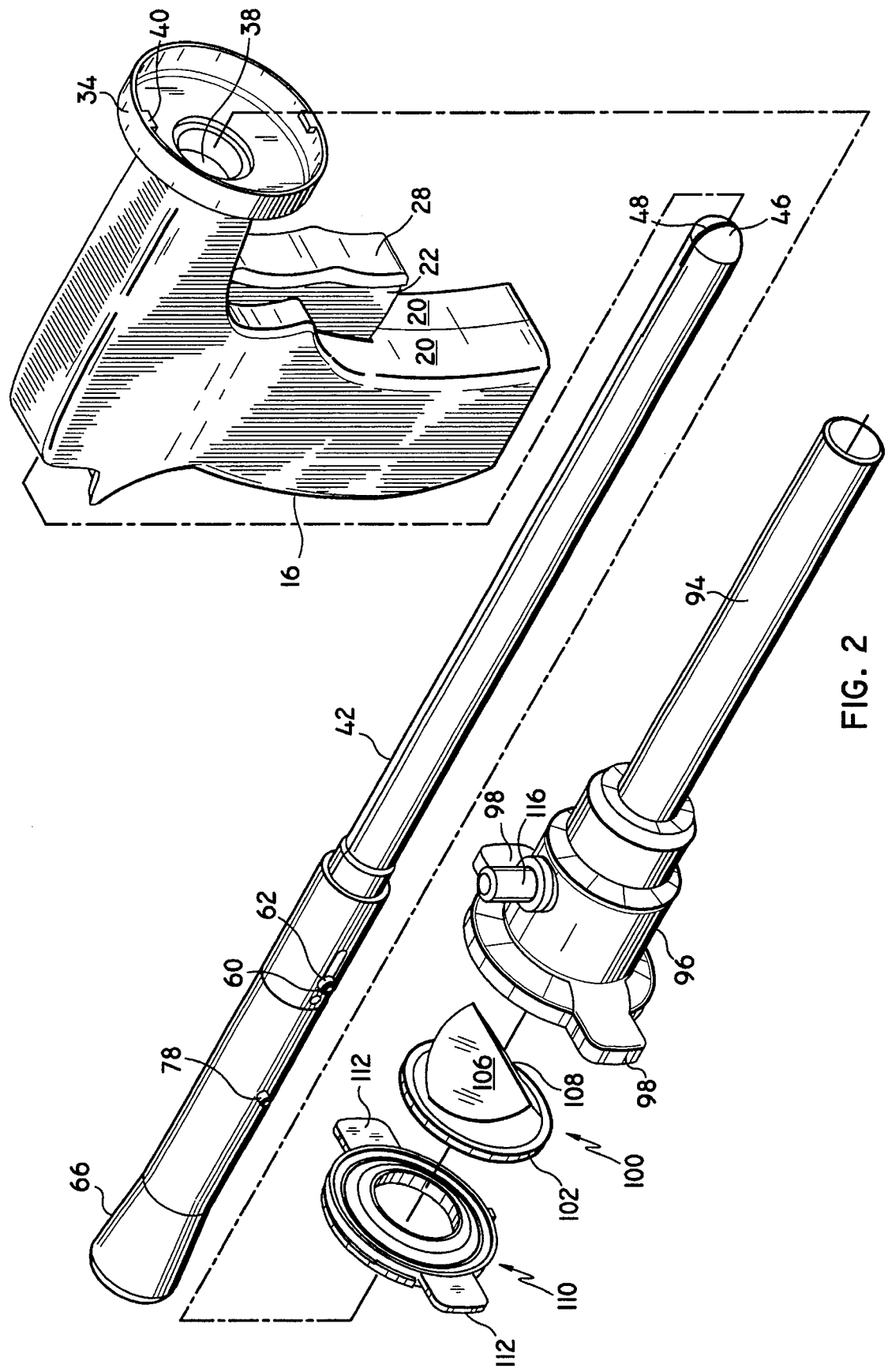
FIG. 2 is a perspective view with parts separated of the surgical trocar of FIG. 1.
Figure 3:
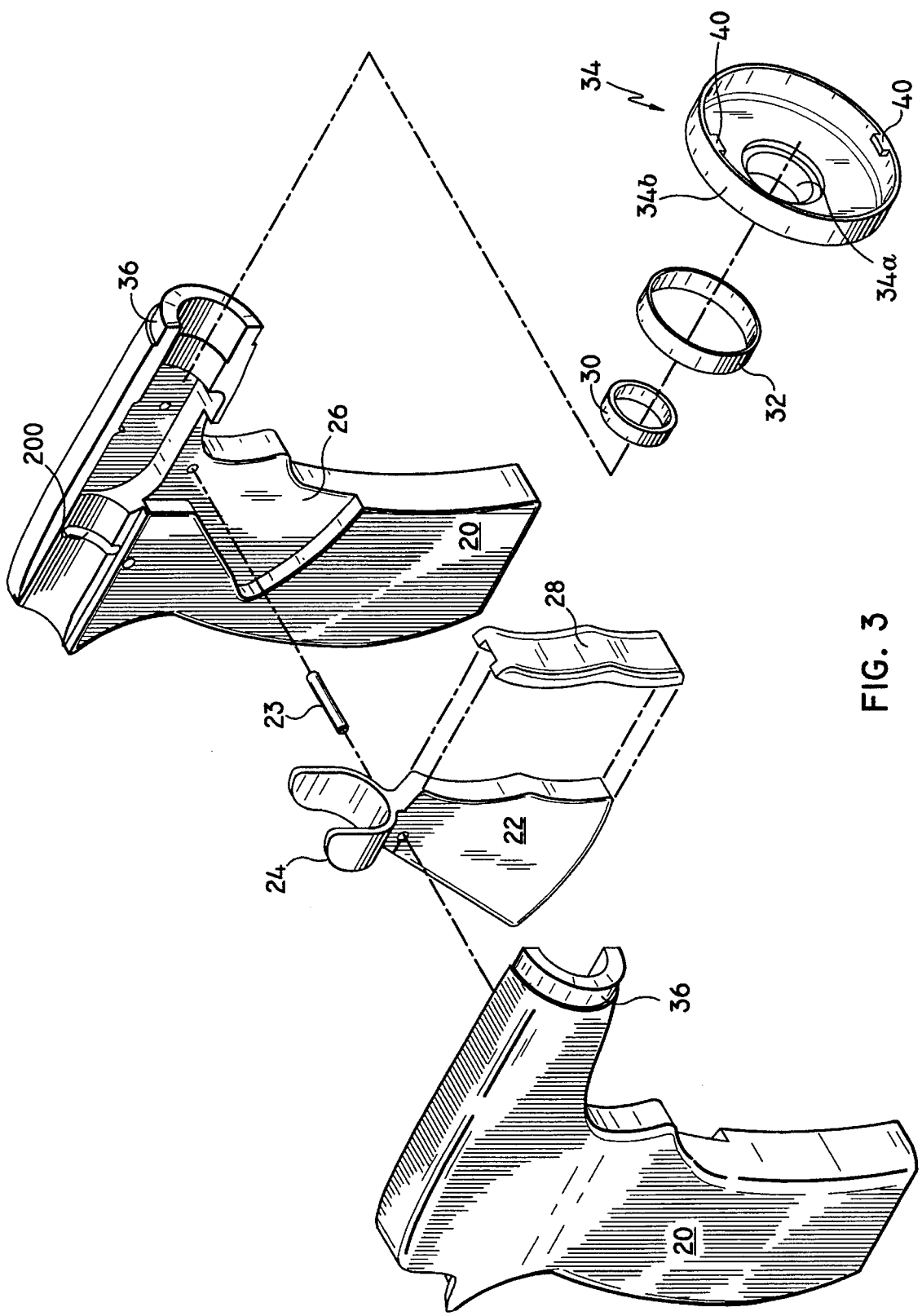
FIG. 3 is a perspective view with parts separated of the handle portion of the obturator assembly.

Referring now to FIGS. 1–3, obturator assembly 14 includes handle 16 and an obturator portion 18 which is operatively connected to the handle 16. Handle 16 includes frame or housing half sections 20 which may be affixed to each other by suitable means such as with adhesives, screws or the like. Half sections 20 are preferably fabricated from any suitable rigid material including polymeric materials, steel, aluminum alloy, and the like. Handle 16 further includes a trigger 22 which is used to actuate obturator portion 18. As best depicted in FIG. 3, trigger 22 is pivotably mounted about pivot pin 23 and possesses an upper portion 24 defining a generally U-shaped configuration. Trigger 22 is accommodated within correspondingly dimensioned recesses 26 formed in housing half sections 20 and possesses a trigger pad 28 positioned over the forward outer surface portion of the trigger 22. Trigger pad 28 defines an enlarged width to enhance grasping of trigger 22 by the surgeon and to distribute the penetrating forces across an enlarged surface area for comfort.

Handle 16 further includes detent spring 30, annular flange 32 and front ring 34. Detent spring 30 is fabricated from a resilient material and functions in maintaining the appropriate relationships and positionings of the components of handle 16 and obturator portion 18 as will be appreciated from the description provided below. Annular flange 32 is positioned about the perimeter of the forward portions of half sections 20 within the annular recess 36 formed in the outer surface of the assembled half sections 20. Annular flange 32 assists in maintaining the handle in an approximated assembled condition.

Front ring 34 is affixed to the forward portion of handle 16 and serves in mounting cannula assembly 12 to obturator assembly 14. Front ring 34 defines a proximal tube mounting portion 34a (FIGS. 3 and 5) and an enlarged distal portion 34b. Tube mounting portion 34a is received within a correspondingly dimensioned axial bore 38 (FIG. 2) defined by the assembled half sections 20. Preferably, the tube mounting portion 34a is adhered to the inner walls of the assembled half sections 20 defining bore 38 to mount the front ring 34 or, in the alternative, may have an external thread which threadably engages an internal thread of the assembled handle half sections 20 to effectuate the mounting. One skilled in the art may readily appreciate other methods for mounting front ring 34 to the handle 16. Front ring 34 further includes two diametrically opposed rib portions 40 extending radially inwardly towards its central axis. Rib portions 40 engage corresponding structure of cannula assembly 12 to detachably mount the cannula assembly 12 to the front ring 34 and handle 16. The particular features of the mounting of cannula assembly 12 with obturator assembly 14 will be discussed hereinbelow.

Figure 4:
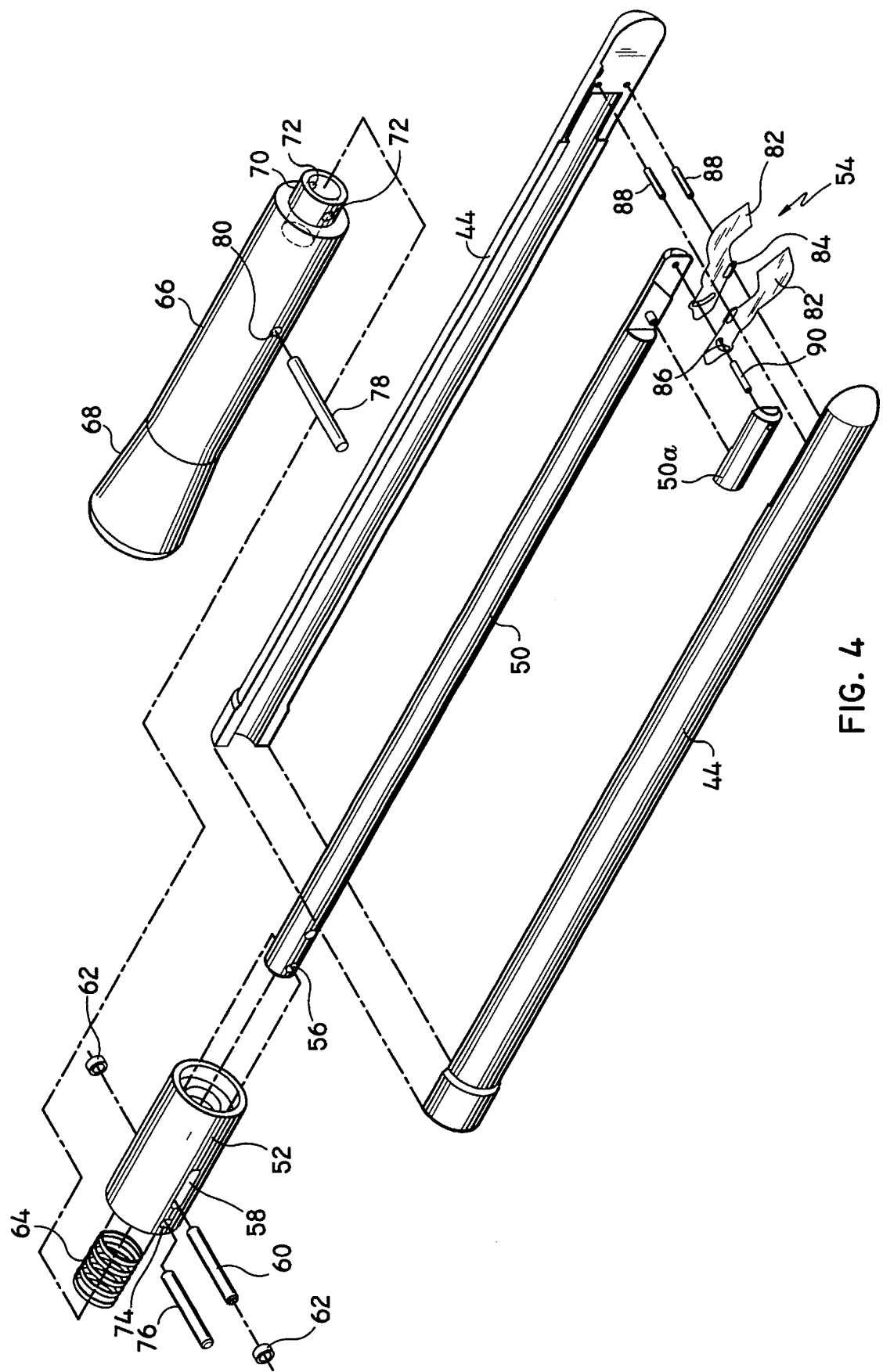
FIG. 4 is a perspective view with parts separated of the obturator portion of the obturator assembly.

Referring now to FIGS. 1, 2 and 4, obturator portion 18 of trocar assembly 10 will be discussed. Obturator portion 18 includes an elongated obturator sleeve 42 consisting of two sleeve half sections 44 adhered to each other along the adjacent surfaces. The distal end of obturator sleeve 42 terminates in a distal rounded portion 46 which is substantially closed except for the provision of a peripheral slot 48. Preferably, distal rounded portion 46 is shaped like a finger tip to facilitate blunt dissection of tissue as will be discussed. Peripheral slot 48 extends through the outer wall portion of obturator sleeve 42 to permit the deployment of a tool mechanism housed therein.

As best depicted in FIG. 4, obturator portion 18 further includes a rod-like drive member 50, a drive collar 52 coaxially mounted about the proximal end portion of the drive member 50 and a tool mechanism, generally identified as reference numeral 54, supported at the distal end portion of the drive member 50. Drive member 50 axially moves within both obturator sleeve 42 and drive collar 52 in response to movement of trigger 22 to retract and deploy tool mechanism 54. The proximal end portion of drive member 50 includes two diametrically opposed apertures 56 formed in its outer wall. Similarly, drive collar 52 includes two diametrically opposed longitudinal slots 58 in its outer wall surface. Longitudinal slots 58 of drive collar 52 and apertures 56 of drive member 50 receive drive pin 60 to slidably mount the drive member 50 within the drive collar 52. A locking collar 62 is positioned on each end of drive pin 60 to maintain the components in the mounted condition. Locking collars 62 may be secured to pin 60 by suitable means such as adhesives or the like. Obturator portion 18 also includes a compression spring 64 which biases trigger 22 to its unactuated position as will be described below.

Referring again to FIGS. 1, 2 and 4, a delivery unit or handle 66 is connected to the proximal end of collar 52. Delivery unit 66 assists in loading and unloading the assembly 10 with obturators of different sizes and functions. Delivery unit 66 proximally extends through the handle 16 in the assembled condition of the instrument. Delivery unit 66 includes a proximal section 68 dimensioned to be grasped by the hands of a surgeon and a distal section 70 having a reduced diameter. Distal section 70 fits within collar 52 and has a pair of diametrically opposed bores 72 formed therein. Similarly, collar 52 has a pair of corresponding diametrically opposed bores 74. A mounting pin 76 traverses bores 72 of delivery unit 66 and bores 74 of collar 52 to operatively connect the two components. Delivery unit 66 further includes a mounting pin 78 which is received within opposed apertures 80 defined in the unit. Mounting pin 78 functions in mounting the obturator portion to handle 14 as will be discussed.

Referring now to FIGS. 4–6, the tool mechanism 54 will be discussed. Drive member 50 includes a tube half portion 50a (FIG. 4) which, when assembled to the main portion of drive member 50, defines a slot or storage area for accommodating tool mechanism 54. Tool mechanism 54 includes two cutting blades 82 mounted in an overlapping manner within the storage area. Cutting blades 82 each include an elongated mounting aperture 84 and a cam slot 86. A mounting pin 88 is received within each mounting aperture 84 and is secured to obturator sleeve 42. A single cam pin 90 is received within cam slots 86 of cutting blades 82 and is mounted to drive member 50 to deploy the cutting blades for cutting action. Cutting blades 82 move in response to movement of drive member 50 and consequent camming action of cam pin 90 within cam slots 86 for deployment and retraction.

Figure 8:
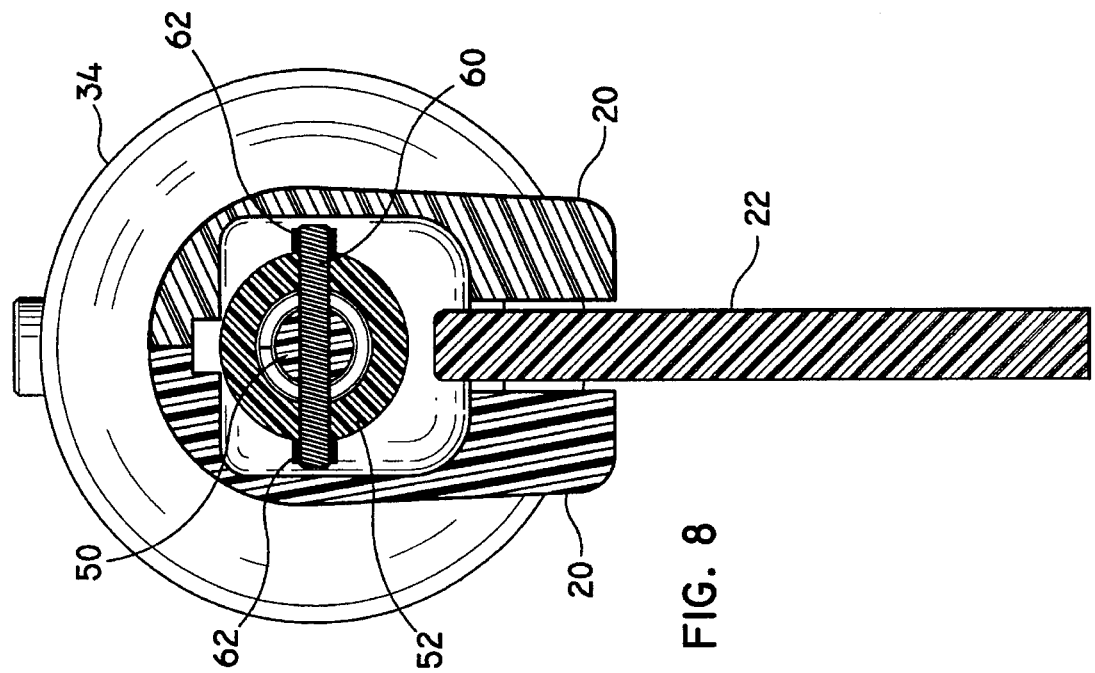
FIG. 8 is a cross-sectional view taken along the lines 8—8 of FIG. 5.
Figure 7:
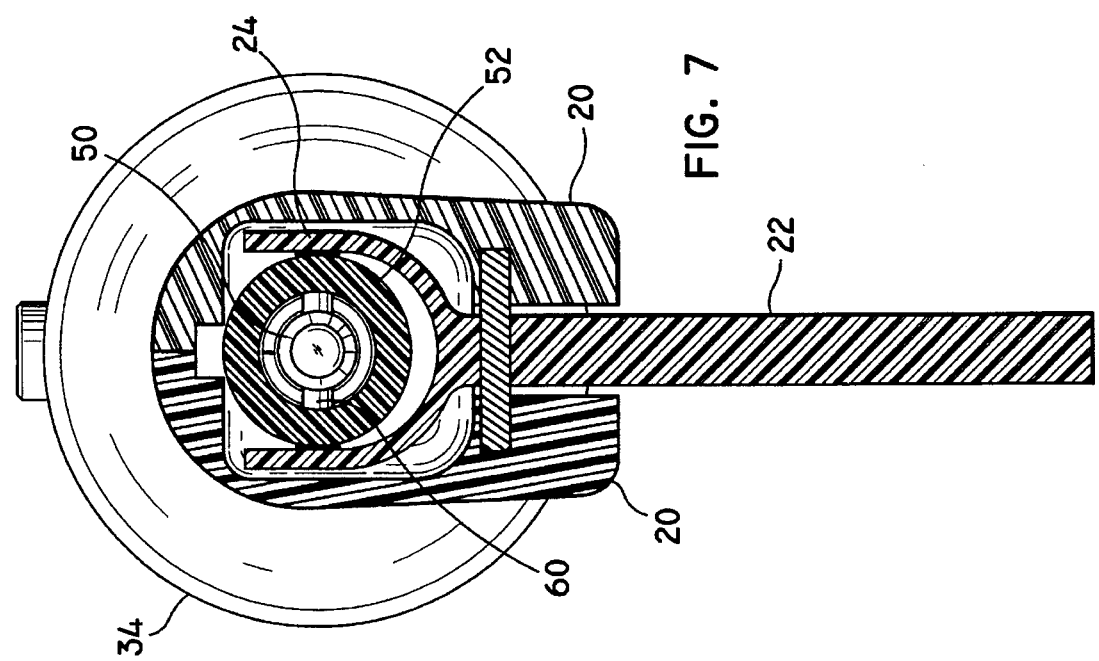
FIG. 7 is a cross-sectional view taken along the lines 7—7 of FIG. 5.

Referring now to FIGS. 5–6, the mechanical interrelationship of the component parts of handle 16 and obturator portion 18 will be discussed in detail. In the assembled condition of obturator portion 18 and handle 16, drive collar 52 and the proximal end portions of obturator sleeve 42 and drive member 50 are disposed within handle 16 as shown in FIG. 5. Detent spring 30 is positioned between the forward end of drive collar 52 and front ring 34. The upper U-shaped portion 24 of trigger 22 is disposed about the outer circumference of drive collar 52 and abuts each locking collar 62 attached to drive pin 60 as best illustrated in FIG. 5 and the cross-sectional views of FIGS. 7 and 8. Thus, depression of trigger 22 translates into distal advancing movement of drive member 50 through the engagement of upper U-shaped portion 24 and locking collars 62. As best shown in FIG. 5, compression spring 64 is positioned about a proximal portion of drive member 50. Compression spring 64 abuts drive pin 60 at its first end and an internal shoulder 92 within drive collar 52 at its other end to normally bias drive member 50 and trigger 22 to its initial unactuated position.

Referring now to FIGS. 1, 2 and 5, cannula assembly 12 of trocar assembly 10 will be described in detail. Cannula assembly 12 includes a cannula sleeve 94 and a cannula housing 96 mounted on one end of the sleeve. Sleeve 94 defines a cannula passage in its interior and may be formed of stainless steel or other rigid materials such as polymeric materials or the like. Cannula housing 96 is rigidly secured to the proximal end of cannula 94 and defines a longitudinal opening for reception and passage of an elongated surgical instrument. The proximal end portion of cannula housing 96 defines a generally circular cross-section and possesses diametrically opposed leg portions 98. A cannula seal 100 fabricated from a resilient material, e.g., rubber, is positioned within the interior of cannula housing 96. Seal 100 includes a circumferential flange portion 102 which rests on a correspondingly dimensioned circumferential ledge 104 within cannula housing 96. Seal 100 generally defines a duck bill shape having two planar tapering portions 106 which intersect at their distal ends to define abutment face or slit 108. Abutment slit 108 permits passage of the elongated object through the seal 100, but in the absence of an instrument, and particularly when cannula assembly 12 is inserted into an insufflated body cavity, abutment slit 108 forms a gas-tight seal that isolates the insufflated cavity from the ambient surroundings. Seal 100 may include at least one, preferably two, reinforcing ribs (not shown) to stabilize the seal. The ribs are preferably positioned to engage the instrument to guide the instrument through slit 108 and prevent piercing of the seal 100 by the tip of the instrument.

Cannula 12 also includes a stabilizing plate 110 (FIG. 2) which is positioned against the flange portion 102 of seal 100 to provide support for the seal during introduction and withdrawal of an elongated instrument. Stabilizing plate 110 includes two diametrically opposed extensions 112 (FIG. 2) which are received within the correspondingly dimensioned leg portions 98 of the cannula housing 96. In the preferred embodiment, stabilizing plate 110 is securely attached to cannula housing 96 at contact points along the extensions of the respective components by spot welding, adhesives or the like. Stabilizing plate 110 also includes a partial external annular rib or thread 114 (FIG. 5) adjacent its proximal end, the function of which will be appreciated from the description below.

A stop cock valve 116 may be incorporated as part of cannula housing 96 to permit the passage of insufflation gases through the cannula sleeve 94 and into the body cavity. A suitable valve for this purpose is available from the Burron OEM Division of B. Braun Medical, Inc. (Model No. 55401022).

Referring now to FIGS. 1 and 5, the mounting of cannula assembly 12 to obturator assembly 14 will be discussed. The cannula assembly 12 is positioned adjacent front ring 34 and manipulated such that rib portions 40 extending radially inwardly from the outer wall of the front ring 34 are proximate partial annular thread 114 of the stabilizing plate 110. Thereafter, cannula assembly 12 is rotated to cause engagement of rib portions 40 of front ring 34 with annular thread 114 of stabilizing plate 110 to detachably mount the cannula 12 to obturator assembly 14 as depicted in FIG. 5. Other means for detachably connecting the cannula assembly 12 to front ring 34 can be readily determined by one skilled in the art such as screw threads, adhesives, bayonet locking, and the like.

OPERATION

The operation of trocar assembly in connection with penetrating the peritoneal cavity during a laparoscopic procedure will now be described. Cannula assembly 12 is mounted to obturator assembly 14 in the aforedescribed manner. The obturator assembly in its unactuated position, i.e., with cutting blades 82 fully enclosed within obturator sleeve 42, is positioned against the patient's abdomen. Thereafter, the surgeon depresses trigger 22 which causes drive member 50 to distally translate in the direction of the arrow shown in FIG. 9. With references to FIG. 10, as drive member 50 moves distally, cutting blades 82 also move distally for a predetermined distance (without any radial outward movement) as provided by the effective axial lengths (i.e., the length along the x-axis) of mounting apertures 84 such that the pointed edges 83 of cutting blades 82 penetrate the skin tissue. Further distal movement of drive member 50 causes further relative movement of the cutting blades 82 whereby the cutting edges 82a of the cutting blades 82 move generally outwardly away from the longitudinal axis of obturator portion 18 as effectuated by the camming action of cam pin 90 within cam slots 86. As cutting blades 82 move outwardly cutting edges 82a of the cutting blades 82 incise the tissue. It is significant to note that pointed ends 83 of cutting blades 82 start at one side of the center line or longitudinal axis of obturator portion 18 and then cross over the center line during deployment thereof. This particular movement of pointed ends 83 ensures that no "tag" or portion of skin is left intact at the center point.

In the fully deployed position of cutting blades 82 shown in FIG. 10 the cutting edges 82a are in general parallel relation with the longitudinal axis of obturator portion 18 Of FIG. 10. Cutting blades 82 generally move outwardly away from the longitudinal axis within the same plane. Thus, the incision formed is linear and has a dimension substantially equal to the distance between the cutting edges 82a.

Once the cutting blades 82 have reached the end of their travel, the surgeon releases trigger 22 which causes rod member 50 to return to its initial proximal position under the influence of compression spring 64 and the blades are retracted. The surgeon can then decide to bluntly dissect with distal rounded portion 46 of obturator sleeve 42 or use the cutting action of the blades 82 for sharp dissection. The trigger 22 is pulled and released as many times as necessary to propagate the incision. At the peritoneal lining, pointed tips 83 aid in piercing the lining in a controlled fashion that does not require a large downward force. Once cutting blades 82 have penetrated the outer skin tissue and the peritoneal lining the trocar assembly 10 may be then advanced into the incision to the desired position. Thereafter, obturator assembly 14 is detached from cannula assembly 12 by rotating the obturator assembly to effectuate disengagement of partial annular rib 114 of stabilizer plate 110 from rib portions 40 of front ring 34 thereby leaving cannula assembly 12 within the incision. Surgical instruments are then introduced into the abdominal cavity through cannula 12 to perform the desired surgery.

The surgical trocar 10 of the present disclosure provides significant advantages over conventional trocar units. Handle 16 may be readily grasped by a single hand of the user and comfortably manipulated about the surgical site. The incision made is substantially linear and, thus, heals more rapidly than arcuate or three lobe incisions formed by conventional trocars. Further, due to the mechanical relationship of the trigger mechanism, drive rod 50 and cutting blades 82, the force required on behalf of the surgeon to incise the abdominal wall is greatly minimized. Moreover, the peritoneal lining can be penetrated with pointed ends 83 of cutting blades 82 without a significant downward force exerted on the trocar 10. In addition, trocar 10 provides the capability of using blunt dissection (i.e., with distal rounded portion 46 of the obturator sleeve 42) as an alternate or in combination with sharp dissection, i.e., with cutting blades 82 exposed.

Figure 11:
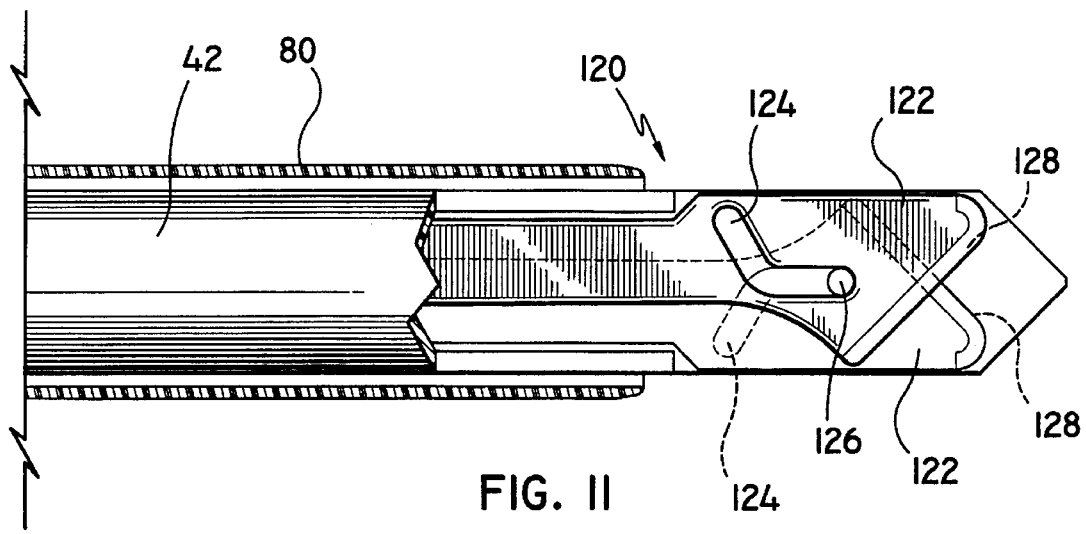
FIGS. 11–13 are side plan views in cross-sections of the distal end of the obturator assembly illustrating an alternative arrowhead cutting blade configuration.
Figure 12:
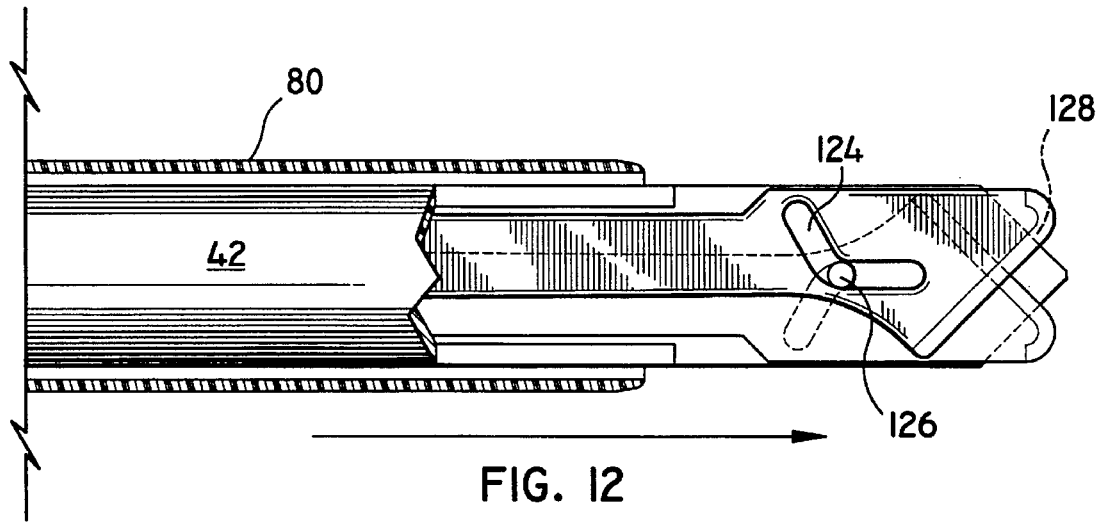
Figure 13:
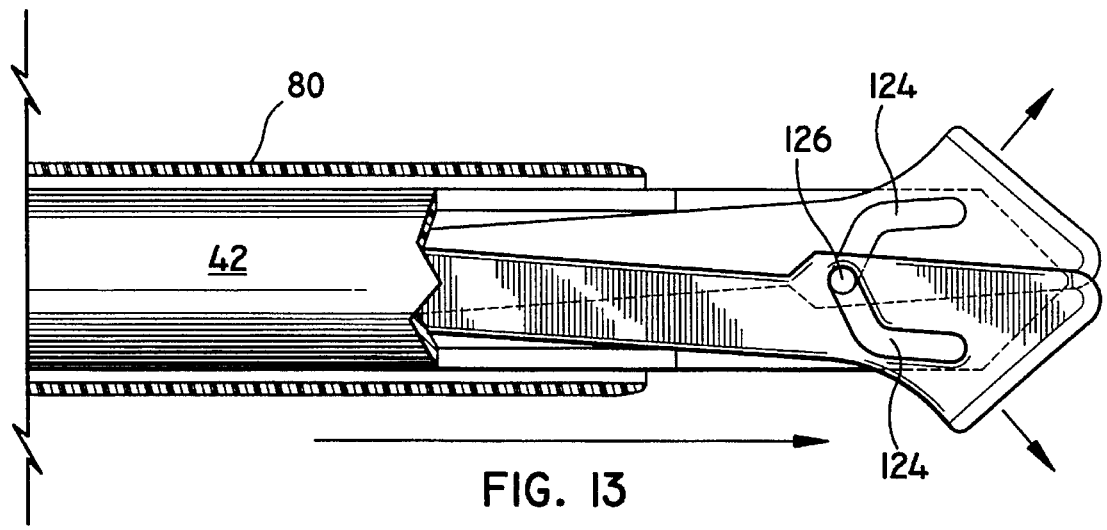

FIGS. 11–13 illustrate an alternative blade structure which can be used with the apparatus 10 of the present disclosure. Blade structure 120 includes two generally arrow-shaped blades 122 arranged in an overlapped or interleaved manner within the obturator sleeve 42. Each blade 122 includes an L-shaped cam slot 124 formed therein which receives single cam pin 126. The cutting blades 122 are mounted to drive member 50 at their proximal ends about a single pin (not shown) which is received within correspondingly dimensioned apertures (not shown) formed in each blade. Cutting blades 122 have cutting edges 128 which define approximately a 25° angle relative to the longitudinal axis of the obturator portion when in the unadvanced position of FIG. 11.

Cutting blades 122 are deployed in a similar manner to the cutting structure of FIG. 1. Distal movement of drive member 50 as effectuated by depression of trigger 22 causes the cutting blades 122 to initially move in a longitudinal direction followed by outward movement away from the longitudinal axis through camming action of cam pin 126 and cam slots 124 to incise the body tissue.

The arrow head blade arrangement provides significant advantages over prior art trocars including the formation of a clean linear incision etc. The sharp pointed ends of the cutting blades 122 facilitate penetrating the peritoneum with minimal insertion force.

Figure 14:
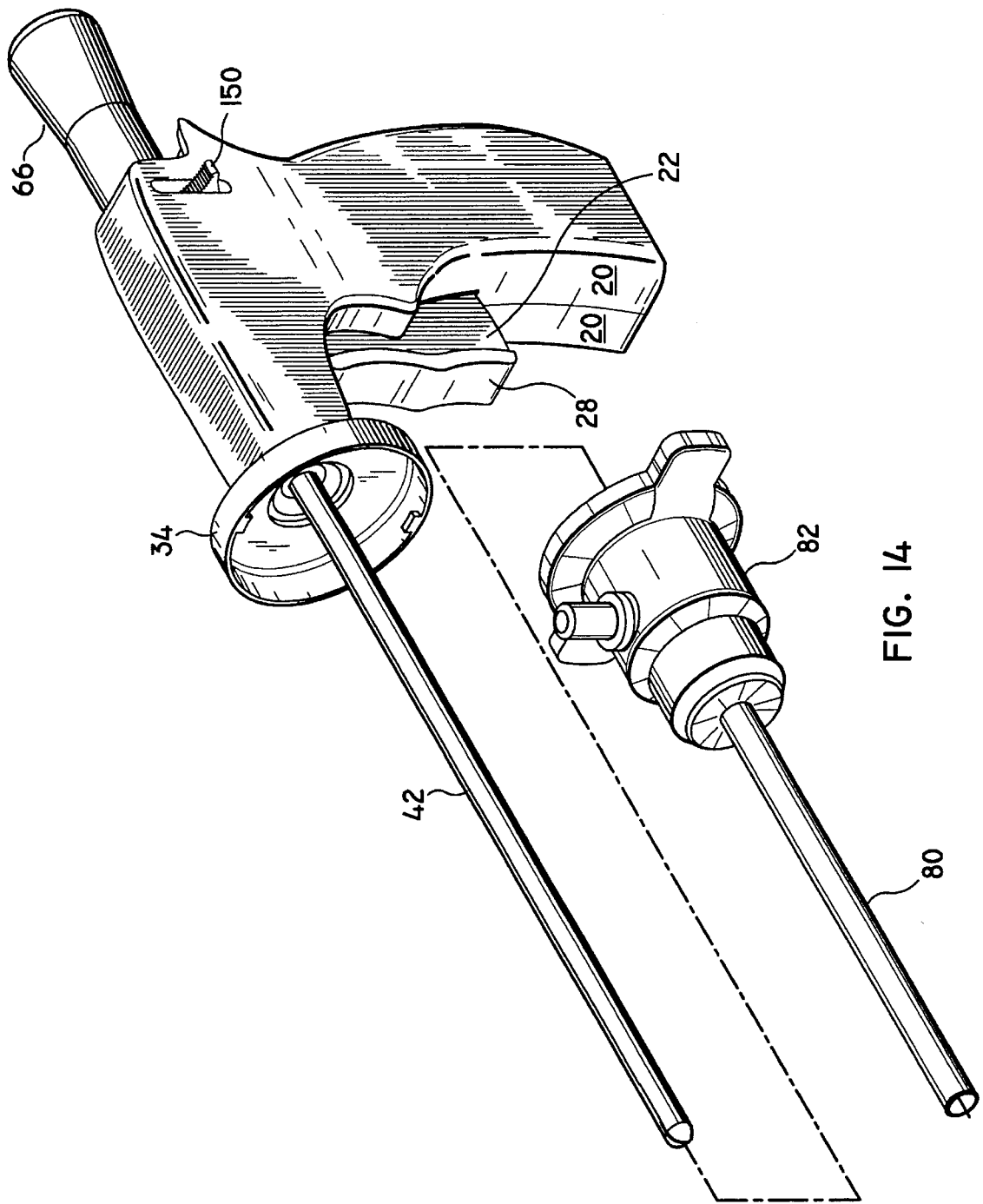
FIG. 14 is a perspective view of an alternative embodiment of the trocar of FIG. 1 illustrating the obturator assembly having a switch mechanism to provide a two step cutting function.
Figures 15, 16:
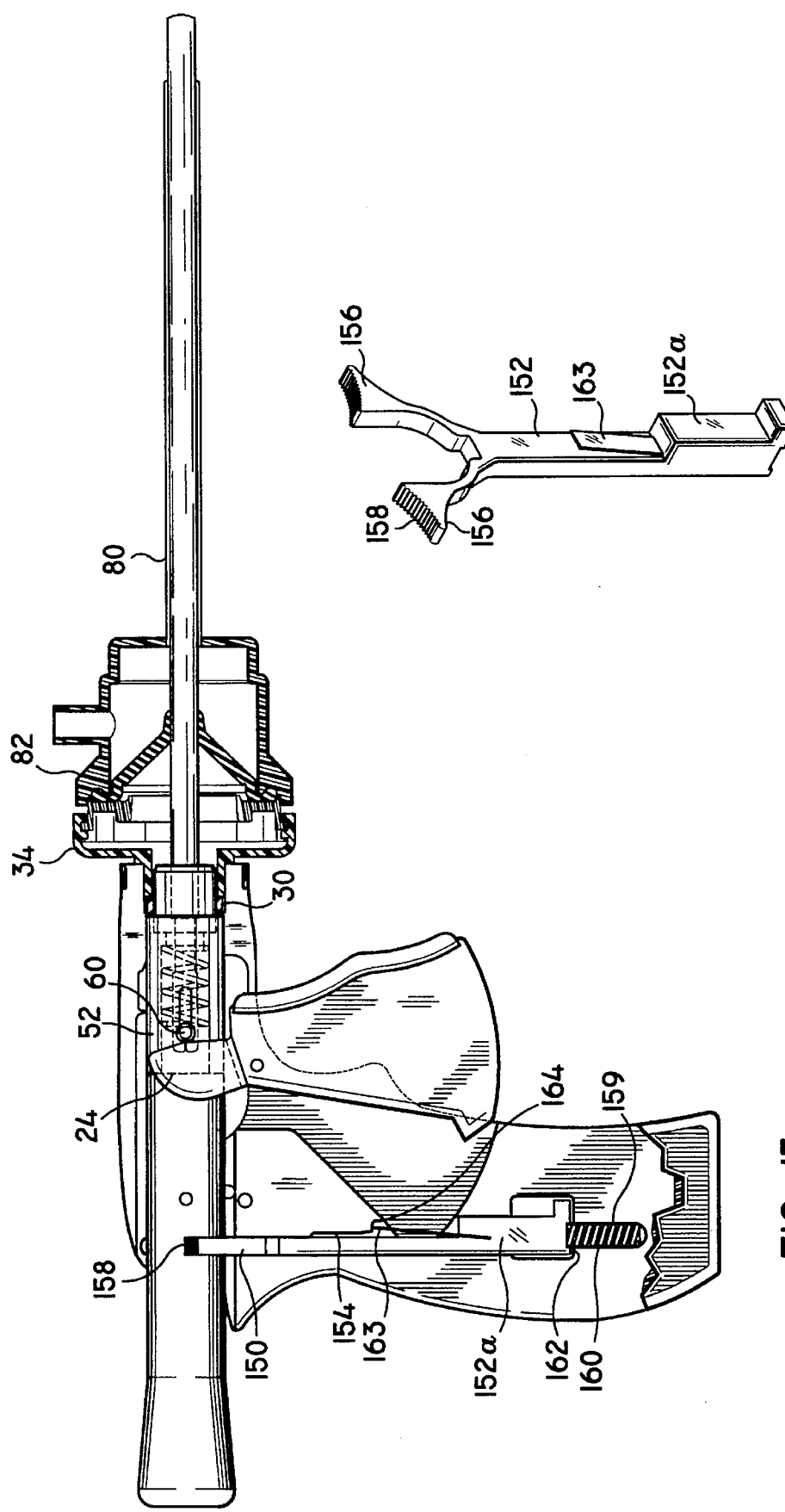
FIG. 15 is a side plan view in partial cross-section of the surgical trocar of FIG. 14 in an initial unactuated position.
FIG. 16 is a perspective view of the switch member of the switch mechanism for providing the two step cutting function.

Referring now to FIGS. 14–16, there is illustrated an alternate embodiment of the present disclosure. The trocar assembly depicted in these figures is similar in most respects to the trocar assembly of FIG. 1. However, in accordance with this embodiment, the obturator assembly incorporates a two-stage cutting operation. In particular, the obturator assembly possesses a switch 150 in its handle which provides for selective movement of trigger 22 and drive member 50 to vary the dimension of the incision formed by the cutting structure. As best shown in FIG. 16, switch 150 includes an elongated portion 152 which is accommodated within a correspondingly dimensioned recess 154 in handle 16 and two opposed finger levers 156 contiguously formed with the elongated portion 152. Finger levers 156 extend outwardly from respective sides of the handle and include knurled contacting surfaces 158 which are engaged by the surgeon. Elongated portion 152 of switch 150 defines a lower portion 152a having a greater width than the remaining portion of the switch. Switch 150 is movable between a downward position (shown in FIG. 15) and an upward position (shown in FIG. 19) to permit selective advancement of drive member 50 and deployment of the cutting structure. Switch 150 is normally biased to its upward position by compression spring 159 which is positioned within a correspondingly dimensioned recess 160 in handle 16 and abuts the lower surface 162 of the switch 150. A lever spring 163 is connected to main portion 152 of switch 150 and extends generally upwardly where it engages abutment surface 164 defined in handle 16 to maintain the switch 150 in the downward position.

Referring to FIGS. 17–18, the cutting blade structure of the trocar of FIG. 14 includes two cutting blades 166 supported at the distal end of obturator sleeve 42. Each blade 166 includes an arcuate cam slot 168 which receives single cam pin 170. Each blade 166 further includes a generally straight mounting slot 172 which receives mounting pin 174 to mount the blades to obturator sleeve 42. The configuration and deployment of cutting blades will be discussed in greater detail below.

In use of the trocar of FIG. 14, the switch 150 is initially positioned in its downward position as shown in FIG. 15. Thereafter, the trocar is positioned against the abdominal wall and trigger 22 is gradually depressed to achieve the fully depressed or pivoted position shown in FIG. 17 to make an initial incision in the outer skin tissue of the abdomen. It is to be noted that in the downward position of switch 150, trigger 22 is capable of achieving its completely depressed position such that rod member 50 is fully distally advanced to fully deploy the cutting blades 166 as shown in FIG. 18. In the fully deployed position of cutting blades 166, the cutting edges 166a are in general parallel relation with the longitudinal axis of the obturator and also extend beyond the outer surface of cannula sleeve 94 as shown in FIG. 18. Thus, in the first stage of the incising process the incision formed in the outer skin tissue is slightly larger than the diameter of the cannula sleeve 94. The surgeon then releases trigger 22 and focuses his attention to completing the incising process by forming an incision in the abdominal wall and peritoneal lining. It is desirable that the incision formed in the peritoneal lining be substantially equal to or slightly less than the outer diameter of cannula sleeve 94 such that a fluid tight seal is formed about the cannula sleeve by the adjacent lining tissue defining the opening. In this regard it is to be noted that during the full depressive movement of trigger 22 (shown in FIG. 17), i.e., the first stage of the incising process, the rear surface 176 of trigger 22 encounters lever spring 163 and moves the lever spring 163 to a position disengaged from abutment surface 164 of handle 16 thereby permitting switch 150 to move to its second upward position under the influence of compression spring 159 as shown in FIG. 19. With switch 150 in the upward position, the second step of the incising process, i.e., incising the abdominal wall and peritoneal lining is performed. Trigger 22 is depressed to deploy the blades. However, in the upward position of the switch 150, trigger 22 is capable of depressive movement only to an intermediate position due to the engagement of rear surface 176 of trigger 22 with the enlarged lower portion 152a of switch 150 as shown in FIG. 19. Consequently, cutting blades 166 are only partially deployed to the position depicted in FIG. 20. In this position, the cutting blades 166 form a linear incision in the peritoneal lining, which possesses a dimension substantially equal to or slightly less than the outer diameter of cannula sleeve 94.

Thus, the switch mechanism of the embodiment of FIGS. 15–20 permits the surgeon to selectively control the dimension of the incision formed by the apparatus by manipulating the switch between its two positions. In summary, with switch 150 in its downward position, the cutting blades 166 are capable of being fully deployable to form an incision in the outer skin of the abdominal wall, which incision is slightly larger than the outer diameter of cannula. With the switch 150 in the upward position, the drive member 50 is only advanceable to an intermediate position. Thus, the cutting blades 166 are only partially deployed to form an incision in the abdominal lining substantially equal to the outer diameter of sleeve 80.

Figure 21:
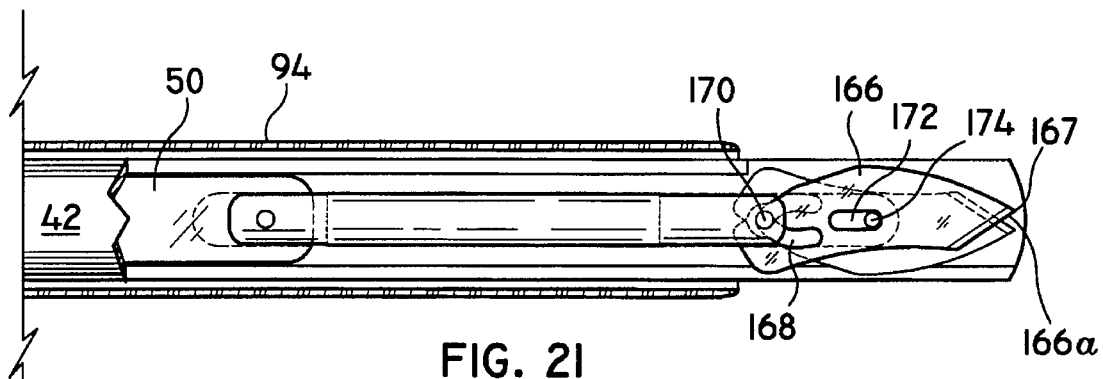
FIGS. 21–24 are cross-sectional views of the distal end of the obturator assembly of FIG. 14 further illustrating deployment of the cutting blades.
Figure 22:
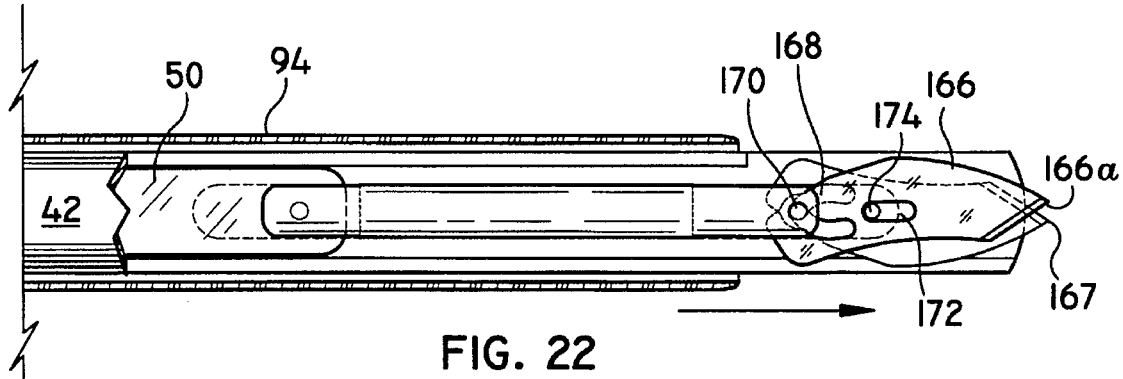
Figure 23:
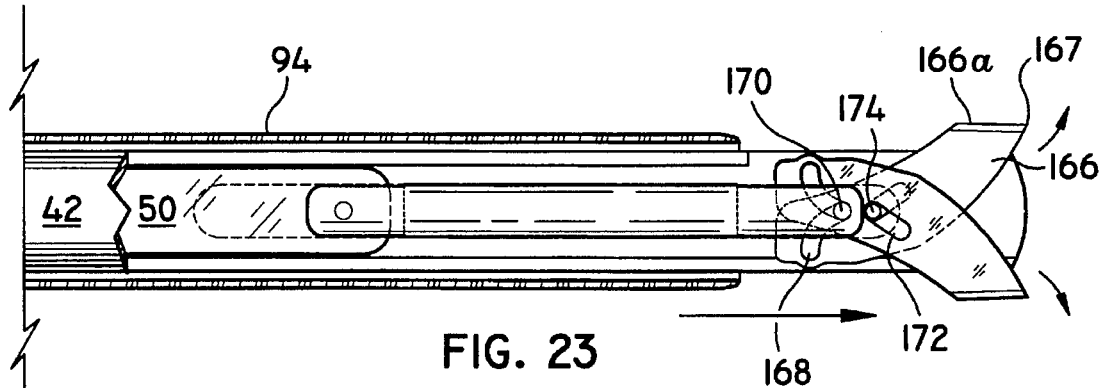
Figure 24:
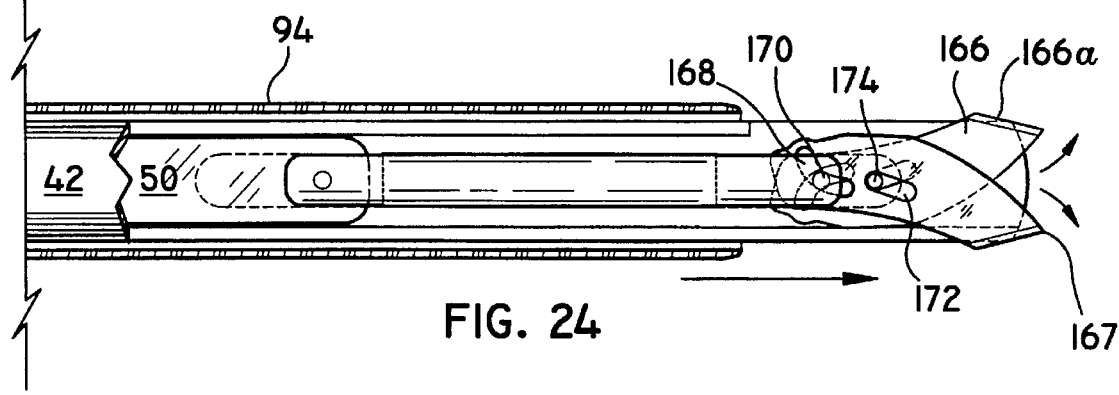

FIGS. 21–24 further illustrate the deployment of cutting blades 166 of the trocar of FIGS. 15–20. FIG. 21 depicts the interleaved or overlapped arrangement of the cutting blades 166 prior to actuation of the trocar within obturator sleeve 42. FIG. 22 shows the position of the blades 166 upon partial depression of trigger 22. In moving to this position, mounting pin 174 traverses mounting slots 172 thereby moving cutting blades 166 distally for a length equal to the length of mounting slot 172. In this position, the pointed tips 167 of cutting blades 166 penetrate the skin tissue. FIG. 23 illustrates the cutting blades 166 fully deployed corresponding to the first stage of the incising process. In achieving this position, the cutting blades 166 first cross over the center line or longitudinal axis of the obturator portion and then continue to move in an outwardly direction away from each other to incise the outer skin tissue as effectuated through the camming action of cam pin 70 and cam slots 168. The initial crossing-over movement of the pointed tips 167 ensures that there is no skin portion or "tag" left at the center point. As illustrated in the drawings, cutting blades 166 pivot about mounting pin 174 whereby cutting edges 166a are in general parallel relation with the longitudinal axis of obturator sleeve 42. FIG. 24 depicts the cutting blades 166 in the intermediate deployed position corresponding to the second stage of the incising process (incising the abdominal wall and peritoneal lining) with switch 150 in the upward position.

It is to be noted that the apparatus can also be used with the switch 150 in its upward position during penetration of the skin tissue and the abdominal lining. In accordance with this use, the dimensions of the incision formed by the cutting blades 166 within the skin tissue and peritoneal lining are the same, i.e., as defined by the spacing of the blade structure as depicted in FIG. 23.

A further feature of the present invention is that both the handle assemblies of FIG. 1 and FIG. 14 can be adapted and attached to various other devices such as ports, trocars etc. to drive the several different functions of the instruments. For example, it is envisioned that the handle assemblies may be readily adapted to be incorporated into the trocar units disclosed in commonly assigned U.S. application Ser. Nos.: 08/132,403, filed Oct. 6, 1993 and 08/322,884 filed Oct. 13, 1993 and commonly assigned U.S. Pat. No. 5,441,041. Further, the handle assemblies may be attached to a variety of different sized obturators, thus, permitting different sized obturators to be actuated with the same handle, thereby increasing flexibility and reducing cost.

Referring now to FIGS. 25–28, the mechanism for mounting the obturator portion 18 to the handle 16 will be described. Half sections 20 each include corresponding L-shaped slots 200 formed in their inner surfaces as shown in phantom in FIGS. 25 and 27 (see also FIG. 3). Half sections 20 include upper and lower recesses formed in their inner surfaces, which, in the assembled condition of the half sections, define upper and lower channels 202 extending within the handle 16 as best depicted in the cross-sectional view of FIG. 26. To load the fully assembled obturator portion 18 within handle 16, obturator portion 18 is appropriately maneuvered such that mounting pin 78 extending through apertures 80 of delivery unit or handle 66 is in a general vertical orientation as shown in FIG. 25. In this position, the mounting pin 78 may be received within the axial bore extending through handle 16 (i.e., portions of mounting pin 78 extending beyond the outer surface of delivery unit 66 are in alignment with the upper and lower channels of handle 16). Obturator portion 18 is advanced within the bore of handle 16 in the direction of the directional arrow shown in FIG. 25. With reference to FIGS. 27–28, obturator portion 18 advances until collar 52 engages detent spring 30. At this position, obturator portion 18 is rotated 90° and released. Release of the obturator portion 18 causes the obturator to move slightly proximally under the influence of detent spring 30 whereby the mounting pin 78 is received within the upper axial section 204 of L-shaped slot 200. It is to be appreciated that detent spring 30 continually biases collar 52 and thus, the entire obturator portion proximally, such that the mounting pin 78 remains within the axial section 204 of L-shaped slot 200, thereby mounting the obturator portion 18 to the handle 16. As further depicted in FIG. 27, the rotation of obturator portion 18 also appropriately positions the locking collar 62 attached to drive pin 60 against U-shaped portion 24 of trigger 22, thus, operatively connecting the trigger 22 to the drive rod 50 of the obturator portion.

While the above description contains many specifics, these specifics should not be construed as limitations on the scope of the invention, but merely as an exemplification of a preferred embodiment thereof. Those skilled in the art will envision other possible variations that are within the scope and spirit of the invention as defined by the claims appended hereto.

What is claimed is:

1. An obturator assembly for penetrating body tissue, which comprises:

a handle assembly including a finger-actuated trigger member;

a sleeve member connected to and extending from the handle assembly;

an obturator shaft at least partially positioned within the sleeve member and engageable with the finger-actuated trigger member of the handle assembly, the obturator shaft defining a longitudinal axis and having proximal and distal end portions; and a cutting mechanism disposed at the distal end portion of the obturator shaft, the cutting mechanism deployable for cutting action upon movement of the trigger member, wherein the obturator shaft is adapted to move distally upon movement of the trigger member to deploy the cutting mechanism from the sleeve member, and wherein the cutting mechanism includes first and second blade members, the blade members at least moveable relative to the longitudinal axis of the obturator shaft between a first non-deployed position wherein the cutting blades are disposed within the obturator sleeve and a second deployed position wherein cutting edges of the cutting blades are displaced from the longitudinal axis and exposed beyond the obturator sleeve.

2. The obturator assembly according to claim 1 wherein the cutting edges of the cutting blades move substantially within a common plane to thereby form a linear incision in body tissue.

3. The obturator assembly according to claim 1 including a camming mechanism for moving the cutting blades between the first non-deployed position and the second deployed position, the camming mechanism including a cam slot formed in each cutting blade and a single cam pin positioned within the cam slots.

4. The obturator assembly according to claim 1 wherein the first and second blade members are supported by the sleeve member.

5. The obturator assembly according to claim 4 wherein the first and second blade members each include a mounting slot wherein a mounting pin is disposed within each mounting slot and connected to the sleeve member to mount the first and second cutting blades to the sleeve member.

6. The obturator assembly according to claim 1 wherein the sleeve member includes a blunt distal end portion, the blunt distal end portion configured to facilitate blunt dissection of tissue.

7. The obturator assembly according to claim 6 wherein the blunt distal end portion of the sleeve member has a slot to permit movement of the first and second blade members between the first non-deployed and the second deployed positions.

8. The obturator assembly according to claim 1 wherein the blade members overlap each other and wherein the cutting edges cross over the longitudinal axis to reach the second deployed position.

9. A surgical trocar, which comprises:

a cannula;

an obturator configured for insertion into the cannula, the obturator including proximal and distal end portions;

at least two overlapping blade members for cutting tissue, the blade members sharing a common pivot point and supported at the distal end portion of the obturator for movement away from the obturator;

an actuating mechanism associated with the obturator and operatively connected to the blade members, the actuating mechanism including a trigger member movable to cause movement of the blade members to a deployed position at least partially exposed beyond the cannula.

10. The surgical trocar according to claim 9, wherein the obturator includes:

an obturator sleeve having proximal and distal end portions; and an obturator shaft at least partially disposed within the obturator sleeve and reciprocally axially movable therewithin.

11. The surgical trocar according to claim 10, wherein the blade members are operatively connected to the obturator shaft.

12. The surgical trocar according to claim 11, wherein the obturator shaft is operatively connected to the trigger member such that movement of the trigger member in one direction causes distal movement of the obturator shaft to move the blade members to the deployed position thereof at least partially exposed beyond a distal end portion of the obturator sleeve.

13. The surgical trocar according to claim 12, wherein the actuating mechanism includes a camming mechanism, the camming mechanism actuable to move the blade members from an initial closed position to an open cutting position wherein cutting edges of each blade are displaced from the longitudinal axis of the obturator sleeve, the camming mechanism including at least one camming pin and at least one cam slot formed in each cutting blade.

14. The obturator assembly according to claim 10 wherein the distal end portion of the obturator sleeve is rounded and is provided with a slot to permit the blade members to move from a non-deployed position within the obturator sleeve to the deployed position outside the obturator sleeve.

15. The surgical trocar according to claim 9, wherein the cannula includes a cannula housing and a cannula sleeve extending from the cannula housing.

16. The surgical trocar according to claim 15, including means for detachably mounting the obturator to the cannula housing of the cannula.

17. A surgical trocar, which comprises:

a cannula; and an obturator configured for at least partial insertion into the cannula and defining a longitudinal axis, the obturator including:

an obturator shaft having proximal and distal end portions, the obturator shaft reciprocally axially movable within the cannula;

at least two blade members supported at a distal end portion of the obturator and moveable between at least a non-deployed position and a fully deployed position in response to movement of the obturator shaft;

a handle operatively connected to the obturator shaft, the handle having a trigger selectively movable to cause reciprocal axial movement of the obturator shaft and movement of the blade members between the non-deployed and fully deployed position; and a manually operable member mounted to the handle and operatively engageable with the trigger, the manually operable member selectively movable between two positions, wherein in a first position of the manually operable member the trigger is capable of moving to a first position thereof corresponding to the fully deployed position of the blade members and wherein in a second position of the manually operable member the trigger is capable of moving to a second position thereof corresponding to a partial deployed position of the blade members, wherein the manually operable member is normally biased to the second position thereof.

18. The surgical trocar according to claim 17 wherein the trigger is pivotally mounted to the handle.

19. The surgical trocar according to claim 18 including a spring member for biasing the manually operable member to the second position thereof.

20. The surgical trocar according to claim 19 including means for retaining the manually operable member in the first position.

21. The surgical trocar according to claim 20 wherein the means for retaining is released upon movement of the trigger to the first position thereof to thereby permit movement of the manually operable member to the second position thereof under the influence of the spring member.

22. The surgical trocar according to claim 21 wherein the means for retaining the manually operable member includes a leaf spring mounted to the manually operable member and engageable with an inner shelf of the handle to retain the manually operable member in the first position.

23. The surgical trocar according to claim 22 wherein the trigger is adapted to engage the leaf spring upon movement of the trigger to the first position thereof to thereby release the leaf spring from its engagement with the inner shelf of the handle to permit movement of the manually operable member to the second position thereof.

24. The surgical trocar according to claim 17 wherein the cannula includes a cannula housing and a cannula sleeve extending from the cannula housing.

25. The surgical trocar according to claim 24 including means for detachably mounting the obturator to the cannula housing of the cannula.

26. The surgical trocar according to claim 17 wherein the cannula has an outer diameter and wherein the blade members in the fully deployed position extend outside the outer diameter of the cannula.

27. The surgical trocar according to claim 26 wherein the blade members in the partial deployed position possess a dimension no greater than the outer diameter of the cannula.

28. A handle system to be connected to a trocar of the type including a cannula having a cannula housing and a cannula sleeve, an obturator configured for at least partial insertion into the cannula and having an obturator shaft and a cutting mechanism associated with a distal end of the obturator shaft, the handle system including:

a frame;

a trigger mechanism associated with the frame for axially moving the obturator shaft to deploy the cutting mechanism beyond the cannula, the trigger mechanism including a trigger pivotally mounted to the frame, the trigger operatively engageable with the obturator shaft and pivotally movable between a first non-pivoted position corresponding to an unarmed position of the cutting mechanism and a second fully pivoted position corresponding to a fully armed position of the cutting mechanism;

a release mechanism for detachably mounting the frame to the cannula housing; and a manually operable member mounted to the frame and engageable with the trigger, the manually operable member selectively moveable between first and second positions thereof and provided with mechanical means for retaining the manually operable member in the first and second positions, wherein in a first position of the manually operable member the trigger is capable of moving to a fully pivoted position corresponding to a fully advanced position of the obturator shaft and fully armed position of the cutting mechanism, wherein in the second position of the manually operable member the trigger is capable of pivoting to an intermediate position thereof corresponding to an intermediate advance position of the obturator shaft and an intermediate armed position of the cutting mechanism, wherein the manually operable member is normally biased to the second position.

29. The handle system according to claim 28 wherein the mechanical means for retaining the manually operable member in the first position includes a lever spring and the mechanical means for retaining the manually operable member in the second position includes a compression spring.

30. A method for forming an incision in body tissue of a patient, comprising the steps of:

positioning an obturator against the body tissue of a patient, the obturator including at least two overlapping blade members at a distal end thereof and sharing a common pivot point;

actuating the obturator such that the blade members are deployed to incise the body tissue, and forming a generally linear incision in the abdominal wall with the deployed blade members.

31. The method of claim 30 wherein the step of actuating includes the step of initially moving the blade members distally such that cutting edges thereof penetrate the body tissue.

32. The method of claim 31 wherein the step of initially moving the blade members distally is succeeded by the step of moving the cutting edges of the blade members outwardly such that the cutting edges are displaced relative to a longitudinal axis of the obturator.

33. The method of claim 32 wherein the step of initially moving the blade members distally includes moving the blade members such that a pointed end of a first blade member and pointed end of second blade member are on opposed sides of an intervening plane and wherein the step of moving the cutting edges of the blade members outwardly includes moving the pointed ends of the first and second blade members to the opposed side.

34. The method of claim 30 wherein the step of forming a generally linear incision includes using only the blade members which together are used to form a single incision which is generally linear.

35. An obturator assembly for penetrating body tissue, which comprises:

a handle assembly including a finger-actuated trigger member;

an obturator sleeve having a proximal end connected to the handle assembly and a rounded distal end having a slot;

an obturator shaft positioned within the sleeve member and engageable with the finger-actuated trigger member of the handle assembly, the obturator shaft defining a longitudinal axis and having proximal and distal portions; and at least two blade members disposed at the distal portion of the obturator shaft and within the rounded distal end of the obturator sleeve in a non-deployed position, wherein initial movement of the trigger member moves the blade members in a distal direction through the slot in the obturator sleeve and wherein further movement of the trigger member causes each of the blade members to move in a different direction in a common plane with respect to each other.

* * * * *